United States Patent [19]

Cantello

[11] Patent Number: 4,665,072
[45] Date of Patent: May 12, 1987

[54] MORPHOLINE DERIVATIVES, COMPOSITIONS AND METHOD OF USE

[75] Inventor: Barrie C. C. Cantello, Coulsdon, England

[73] Assignee: Beecham Group p.l.c., Great Britain

[21] Appl. No.: 865,348

[22] Filed: May 21, 1986

Related U.S. Application Data

[62] Division of Ser. No. 666,818, Oct. 31, 1984, Pat. No. 4,607,033.

[51] Int. Cl.$^4$ ............... A61K 31/535; C07D 265/30; C07D 413/04
[52] U.S. Cl. .................................. 514/237; 544/153; 544/162
[58] Field of Search ................ 544/153, 162; 514/237

[56] References Cited

U.S. PATENT DOCUMENTS 4,214,081  7/1980  Krapcho ........................... 544/162

Primary Examiner—Robert W. Ramsuer
Attorney, Agent, or Firm—Hopgood, Calimafde, Kalil, Blaustein & Judlowe

[57] ABSTRACT

Compounds of formula (I):

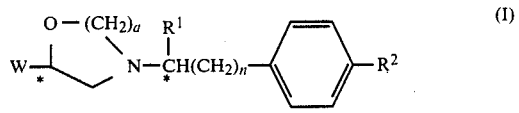

or a salt thereof, in which

W is phenyl optionally substituted by halogen or trifluoromethyl, or a benzofuran-2-yl group,
$R^1$ is hydrogen or methyl,
$R^2$ is carboxyl or a group O—Z—CO$_2$H or an ester or amide thereof; a group O—E—NR$^3$R$^4$ or a group O—E—OR$^5$, wherein $R^3$, $R^4$ and $R^5$ each represents hydrogen or C$_{1-6}$ alkyl, Z is a C$_{1-6}$ straight or branched alkylene chain, n is 1 or 2, a is 2 or 3, and E is a C$_{2-7}$ straight or branched alkylene chain with at least two carbon atoms separating the two heteroatoms in the group $R^2$; a process for the production of such compounds and their use in medicine as anti-hyperglycaemic and/or anti-obesity agents.

8 Claims, No Drawings

MORPHOLINE DERIVATIVES, COMPOSITIONS AND METHOD OF USE

This application is a division of application Ser. No. 666,818 filed Oct. 13, 1984, now U.S. Pat. No. 4,607,033.

The present invention relates to derivatives of 2-phenylmorpholine and related compounds which have anti-hyperglycaemic and/or anti-obesity activity, to processes for their production and their use in medicine.

UK Patent Specification No. 1,394,001 discloses compounds of general formula:

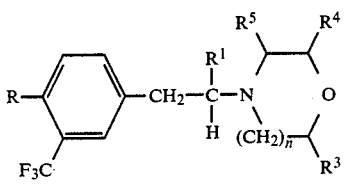

where
R represents a hydrogen or halogen atom;
$R^1$ represents a lower alkyl group;
$R^3$ and $R^4$ represent a hydrogen atom, a lower alkyl group or a phenyl group;
$R^5$ represents a hydrogen atom or a lower alkyl group; and
n is 1 or 2;
and the non-toxic addition salts of such compounds, having anorectic activity, which are useful as appetite suppressants. We have discovered a class of novel 2-phenylmorpholine derivatives having anti-hyperglycaemic and/or anti-obesity activity.

According to the present invention there is provided a compound of formula (I):

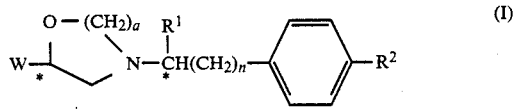

or a salt thereof, in which
W is phenyl optionally substituted by halogen or trifluoromethyl, or a benzofuran-2-yl group,
$R^1$ is hydrogen or methyl,
$R^2$ is carboxyl or a group O—Z—CO$_2$H or an ester or amide thereof; a group O—E—NR$^3$R$^4$ or a group O—E—OR$^5$,
wherein $R^3$, $R^4$ and $R^5$ each represents hydrogen or $C_{1-6}$ alkyl, Z is a $C_{1-6}$ straight or branched alkylene chain, n is 1 or 2, a is 2 or 3, and E is a $C_{2-7}$ straight or branched alkylene chain with at least two carbon atoms separating the two heteroatoms in the group R$^2$.

Preferably $R^1$ is methyl.
Preferably n is 1.
Preferably Z is CH$_2$ and preferably E is CH$_2$CH$_2$.

When $R^2$ is an ester, preferred esters are $C_{1-6}$ alkyl esters thereof, particularly the methyl or ethyl esters.

When $R^2$ is an amide, preferred amides are those wherein $R^2$ is modified to a group CONR$^3$R$^4$ or a group O—Z—CONR$^3$R$^4$, wherein each of R$^3$ and R$^4$ is hydrogen or $C_{1-6}$ alkyl.

In one aspect of the invention the salts of compounds of formula (I) are preferably pharmaceutically acceptable salts.

Pharmaceutically acceptable salts of compounds of formula (I) include acid addition salts formed with a pharmaceutically acceptable acid such as hydrochloric acid, hydrobromic acid, orthophosphoric acid, sulphuric acid, methane sulphonic acid, toluenesulphonic acid, acetic acid, propionic acid, lactic acid, citric acid, fumaric acid, malic acid, succinic acid, salicylic acid or acetylsalicylic acid.

Pharmaceutically acceptable carboxylic acid salts of compounds of formula (I) include metal salts such as aluminium, alkali metal salts such as sodium, potassium, or lithium, alkaline earth metal salts such as calcium or magnesium, and ammonium or substituted ammonium salts, for example those with lower alkylamines such as triethylamine.

When $R^1$ is methyl, the compounds of formula (I) have two asymmetric carbon atoms, marked with asterisks in the formula. These compounds may, therefore, exist in four stereoisomeric forms. The present invention encompasses all stereoisomers of the compounds of formula (I) whether free from other stereoisomers or admixed with other stereoisomers in any proportion and thus includes, for instance, racemic mixtures of enantiomers.

When W is optionally substituted phenyl compounds of formula (I) preferably have the R,R-configuration.

The absolute configuration of any compound of formula (I) may be determined by conventional X-ray crystallographic techniques.

The present invention also provides salts of compounds of formula (I) that are not pharmaceutically acceptable as they are also useful in the preparation of other compounds of formula (I).

Compounds of formula (I) may be prepared by reacting a compound of formula (II)

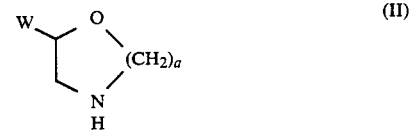

wherein W and a are as defined in relation to formula (I) or an acid addition salt thereof, with a compound of formula (III)

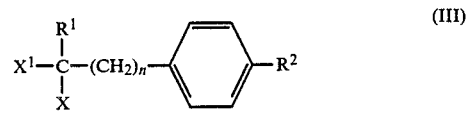

wherein $R^1$, $R^2$ and n are as defined in relation to formula (I) and X is halogen or an alkylsulphonyloxy or arylsulphonyloxy group and $X^1$ is hydrogen, or X and $X^1$ together represent oxo.

Preferably X is chlorine or a p-toluenesulphonyloxy group when $X^1$ is hydrogen.

When a compound of formula (II) is reacted with a compound of formula (III) wherein X and $X^1$ together represent oxo the reaction is usually carried out in the presence of a reducing agent such as sodium cyanoborohydride. The reaction is conveniently effected in a lower alkanolic solvent such as methanol or ethanol at from 0° to 20° C.

When a compound of formula (II) is reacted with a compound of formula (III) wherein X is halogen or an alkylsulphonyloxy or arylsulphonyloxy group, and $X^1$ is hydrogen the reaction is generally carried out in the presence of an organic base, suitably a tertiary amine such as triethylamine. The reaction is conveniently carried out in a lower alkanolic solvent such as ethanol, heated to reflux.

Compounds of formula (I) may also be prepared by cyclisation of a compound of formula (IV)

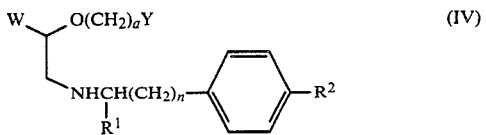

wherein W, $R^1$, and $R^2$, a and n are as defined in relation to formula (I), and Y is hydroxyl or halogen.

When Y is halogen the cyclisation reaction is generally effected in the presence of an inorganic base such as potassium carbonate in an organic solvent such as acetone, suitably at elevated temperatures.

When Y is hydroxyl the cyclisation is generally conducted in the presence of a conventional dehydrating reagent such as sulphuric acid.

Compounds of formula (I) may also be prepared by reducing a double bond of a compound of formula (V) or a salt, thereof,

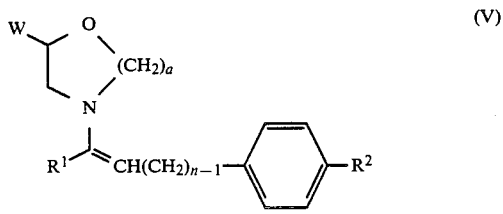

wherein
W, $R^1$, $R^2$, a and n are as defined in relation to formula (I),
and optionally thereafter forming salt of the compound of formula (I) so formed, and/or converting the compound of formula (I) so formed into a further compound of formula (I). The reduction of a compound of formula (V) may be effected by conventional catalytic methods.

The reduction is generally conducted in a suitable solvent such as a lower alkanol, for example ethanol, in the presence of a catalyst such as palladium on charcoal, preferably at an elevated temperature and pressure.

Compounds of formula (I) wherein $R^2$ is not carboxyl may be prepared by reacting a compound of formula (VI):

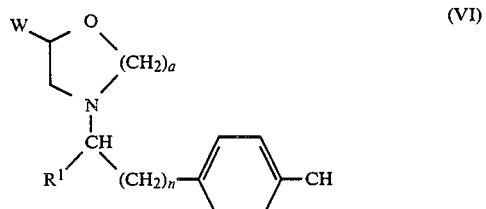

wherein $R^1$, W, a and n are as defined in relation to formula (I), with a compound of formula (VII):

$$X^2-T \qquad (VII)$$

wherein $X^2$ is a leaving group, such as halogen, especially bromine, or tosyloxy; T is $-Z-CO_2R^6$ or $-E-NR^3R^4$ or $-E-OR^7$ wherein Z, E, $R^3$ and $R^4$ are as defined in relation to formula (I), $R^6$ is a carboxy protecting group and $R^7$ is $R^5$ preferably when $R^5$ is $C_{1-6}$ alkyl; and optionally thereafter carrying out one or more of the following steps:

(a) removing any protecting group $R^6$;
(b) converting a group $-O-Z-CO_2H$ to an ester or amide thereof;
(c) forming a salt of a compound of formula (I);
(d) converting a compound of formula (I) into a further compound of formula (I).

The reaction is suitably effected in the presence of an inorganic base such as potassium carbonate in an organic solvent such as acetone, suitably at elevated temperatures.

The group $R^6$ may be any carboxy protecting group conventionally used in the art. In a preferred form of the process T is $-Z-CO_2R^6$, preferably $R^6$ is methyl.

Compounds of formula (VI) may be prepared by treating a compound of formula (VIII):

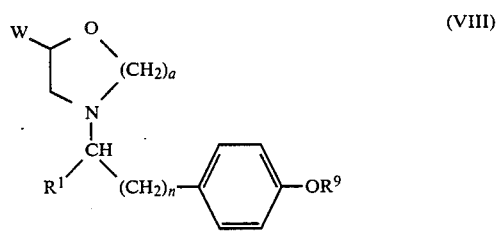

wherein W, $R^1$, a and n are as defined in relation to formula (I) and $R^9$ is a $C_{1-6}$ alkyl group, preferably a methyl group, with an inorganic acid, preferably hydrobromic acid. Alternatively, compounds of formula (VI) may be prepared by catalytic hydrogenolysis of compounds of formula (VIII) wherein $R^9$ is benzyl.

Suitable catalysts include noble metal catalysts such as palladium, for example palladium on charcoal or the like such as platinum for example as platinum oxide. If platinum is used as catalyst an atmospheric pressure of hydrogen may be employed. The reaction may be carried out at any convenient non-extreme temperature but it is generally most suitable to use an ambient or a slightly super ambient temperature such as 30° C. to 100° C., for example 40° C. to 80° C. The hydrogenolysis may be carried out in a conventional hydrogenolysis solvent such as a lower alkanol, for example ethanol.

In a preferred form of the process the compound of formula (VI) is not isolated and is converted in-situ to a compound of formula (I) as hereinbefore described.

The compounds of formula (VIII) may be prepared by processes analogous to those described in UK Pat. No. 1,138,405.

Compounds of formula (I) may be converted into further compounds of formula (I) by conventional processes. Thus, for example an ester of a compound of formula (I), wherein $R^2$ is a carboxyl group or a group $O-Z-CO_2H$, may be treated with an alkylamine to produce the respective amide. Suitably a methyl ester of a compound of formula (I) may be converted to a methyl amide of a compound of formula (I) by treating with methylamine in a lower alkanolic solvent such as methanol, preferably at reflux.

Compounds of formula (I) may be prepared by procedures analogous to those described in UK Pat. No. 1,394,001.

The acid addition salts of compounds of formula (I) may be produced by treating the compound of formula (I) with the appropriate acid.

Compounds of formula (I) and salts, thereof, produced by the above processes, may be purified by conventional methods.

Compounds of formulae (II) and (III) are known compounds or can be prepared from known compounds by using conventional procedures.

Compounds of formula (IV) wherein Y is halogen may be prepared by treating a compound of formula (IV) wherein Y is hydroxyl with a suitable reagent, such as thionyl chloride in an organic solvent such as toluene.

Compounds of formula (IV) wherein Y is hydroxyl are known from UK Patent Application No. 8322137 or can be prepared by procedures analogous to those described in the UK Patent Application.

Compounds of formula (V) may be prepared by reacting a compound of formula (II) with a compound of formula (III) wherein X together with $X^1$ represents oxo. The reaction is generally carried out in the presence of a suitable catalyst such as p-toluenesulphonic acid, in an inert organic solvent such as benzene, usually under Dean and Stark conditions.

Enantiomers of compounds of formula (I) may be prepared by resolving a mixture of stereochemical isomers of a compound of formula (I) by conventional means, such as by the use of an optically active acid as a resolving agent.

Suitable optically active acids which may be used as resolving agents are described in 'Topics in Stereochemistry', Vol. 6, Wiley Interscience, 1971, Allinger, N. L., and Eliel, W. L. Eds.

A compound of formula (I) or a pharmaceutically acceptable salt thereof (hereinafter 'the drug') may be administered as the pure drug, however, it is preferred that the drug be administered as a pharmaceutical composition also comprising a pharmaceutically acceptable carrier.

Accordingly, the present invention also provides a pharmaceutical composition comprising a compound of formula (I) or a pharmaceutically acceptable salt thereof with a pharmaceutically acceptable carrier therefor.

As used herein the term 'pharmaceutical composition' and 'pharmaceutically acceptable' embrace compositions and ingredients for both human and veterinary use.

Usually the compositions of the present invention will be adapted for oral administration although compositions for administration by other routes, such as by injection are also envisaged.

Particularly suitable compositions for oral administration are unit dosage forms such as tablets and capsules. Other fixed unit dosage forms, such as powders presented in sachets, may also be used.

In accordance with conventional pharmaceutical practice the carrier may comprise a diluent, filler, disintegrant, wetting agent, lubricant, colourant, flavourant or the like.

Typical carriers may, therefore, comprise such agents as microcrystalline cellulose, starch, sodium starch glycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.1 to 1000 mg of the drug, more usually 0.1 to 500 mg and favourably 0.1 to 250 mg.

Within the above indicated dosage range, no adverse toxicological effects have been observed with the pharmaceutical acceptable compounds of the invention.

The present invention further provides a method for treating hyperglycaemia in a human or non-human animal which method comprises administering an effective, non-toxic amount of a compound of formula (I) or a pharmaceutically acceptable salt, thereof to a hyperglycaemic human or non-human animal.

The present invention further provides a method for treating obesity in human or non-human animals, which method comprises administering an effective, non-toxic amount of a compound of formula (I) or a pharmaceutically acceptable salt, ester or amide thereof to an obese human or non-human animal.

Conveniently, the drug may be administered as a pharmaceutical composition as hereinbefore defined, and this forms a particular aspect of the present invention.

In treating hyperglycaemic or obese humans the drug may be taken in doses, such as those described above, one to six times a day in a manner such that the total daily dose for a 70 kg adult will generally be about 0.1 to 6000 mg, and more usually about 1 to 1500 mg.

In treating hyperglycaemic or obese non-human animal, especially dogs, the drug may be administered by mouth, usually once or twice a day and at about 0.025 mg/kg to 25 mg/kg, for example 0.1 mg/kg to 20 mg/kg.

The invention will now be illustrated with reference to the following Examples.

In the Examples the substituents in formula (I) are as shown in the following Table.

| Example No. | W | a | $R^1$ | $R^2$ | n | salt |
|---|---|---|---|---|---|---|
| 1 | $C_6H_5$ | 2 | $CH_3$ | $OCH_2CO_2CH_3$ | 1 | HCl |
| 2 | $C_6H_5$ | 2 | $CH_3$ | $OCH_2CONHCH_3$ | 1 | HCl |
| 3 | $C_6H_5$ | 2 | $CH_3$ | $CO_2CH_3$ | 1 | HCl |
| 4 | 3-$CF_3$—$C_6H_4$ | 2 | $CH_3$ | $OCH_2CO_2CH_3$ | 1 | HCl |
| 5 | 3-$CF_3$—$C_6H_4$ | 2 | $CH_3$ | $OCH_2CONHCH_3$ | 1 | HCl |
| 6 | 3-Cl—$C_6H_4$ | 2 | $CH_3$ | $OCH_2CO_2CH_3$ | 1 | HCl |
| 7 | 3-Cl—$C_6H_4$ | 2 | $CH_3$ | $OCH_2CO_2CH_3$ | 1 | HCl |
| 8 | 3-Cl—$C_6H_4$ | 2 | $CH_3$ | $OCH_2CONHCH_3$ | 1 | 2HCl |
| 9 | 3-Cl—$C_6H_4$ | 2 | $CH_3$ | $OCH_2CH_2NHCH_3$ | 1 | 2HCl |
| 10 | 3-Cl—$C_6H_4$ | 3 | $CH_3$ | $OCH_2CO_2CH_3$ | 1 | HCl |
| 11 | benzo-furan-2-yl | 2 | $CH_3$ | $OCH_2CO_2CH_3$ | 1 | HCl |
| 12 | benzo-furan-2-yl | 2 | $CH_3$ | $OCH_2CO_2CH_3$ | 1 | HCl |

-continued

| Example No. | W | a | R¹ | R² | n | salt |
|---|---|---|---|---|---|---|
| 13 | 3-Cl—C₆H₄ | 2 | H | OCH₂CO₂CH₃ | 1 | HCl |

EXAMPLE 1

4-[2-(2-Phenylmorpholino)propyl]phenoxyacetic acid methyl ester hydrochloride

A mixture of 2-phenylmorpholine hydrochloride (6.05 g), 1-(4-carbomethoxymethoxyphenyl)propan-2-one (6.63 g) and sodium cyanoborohydride (1.61 g) in methanol (100 ml) was stirred at room temperature for 22 hours. The solvent was removed under reduced pressure and aqueous sodium bicarbonate solution added to the residue and extracted with dichloromethane (X2). The extracts were washed with aqueous sodium bicarbonate, dried over anhydrous magnesium sulphate, filtered and the filtrate evaporated to dryness to give an oil. Chromatography on silica gel in 0→7% methanol in dichloromethane gave an oil which was dissolved in diethyl ether and treated with an ethereal solution of hydrogen chloride. Evaporation to dryness and trituration of the residue with ethyl acetate gave a solid. Recrystallisation of this solid gave the title compound, m.p. 187°–190° C. (methanol-ethyl acetate), of analytical purity.

¹H nmr δ(DMSO—d₆); 1.15 (3H, d), 2.6–3.65 (7H, m), 3.70 (3H, s), 4.2 (2H, m), 4.75 (2H, s), 5.15 (1H, d), 6.9 (2H, d), 7.25 (2H, d), 7.3–7.6 (5H, m), 12.0 (1H, broad; exchanges with D₂O).

The mother liquors from the above crystallisation were evaporated to dryness and subsequently used in Example 2.

EXAMPLE 2

4[2-(2-phenylmorpholino)propyl]phenoxy N-methylacetamide hydrochloride

To a solution of 4-[2-(2-phenylmorpholino)propyl]phenoxyacetic acid methyl ester hydrochloride (3.0 g; obtained from the mother liquors of Example 1) in methanol (50 ml) was added a 30% aqueous solution of methylamine (10 ml). This mixture was heated under reflux for 3 hours during which time 3 further 10 ml portions of the methylamine solution were added. The solution was cooled to room temperature, a further 10 ml portion of methylamine solution added, and the reaction mixture allowed to stand at room temperature overnight. The solvent was removed under vacuum, aqueous sodium carbonate added to the residue and extracted with dichloromethane (X2). The combined extracts were washed with brine (X2), dried over anhydrous magnesium sulphate, filtered and the filtrate evaporated to dryness. Chromatography of the residue on silica gel in 2% methanol-dichloromethane gave an oil, which, on treatment with an ethereal solution of hydrogen chloride, gave the title compound, m.p. 127°–130° C. (methanol-ethyl acetate-diethyl ether), as a 12:88 mixture of diastereoisomers.

¹H nmr δ(DMSO—d₆): 1.15 (3H, d), 2.5–2.8 (4H, d on m), 2.8–3.8 (6H, m), 4.0–4.25 (2H, m), 4.4 (2H, s), 5.15 (1H, d), 6.8–7.0 (2H, d), 7.05–7.25 (2H, d), 7.25–7.5 (5H, m), 8.05 (1H, broad; exchanges with D₂O), 12.0 (1H, broad; exchanges with D₂O).

EXAMPLE 3

4-[2-(2-Phenylmorpholino)propyl]benzoic acid methyl ester hydrochloride hemihydrate A mixture of 2-phenylmorpholine (1.38 g), 1-(4-carbomethoxyphenyl)propan-2-ol 4-toluene sulphonate (2.95 g) and triethylamine (2 ml) in ethanol (20 ml) was heated under reflux for 21 hours, cooled, concentrated under reduced pressure, poured into aqueous sodium carbonate solution and extracted with ethyl acetate (X2). The combined extracts were washed with brine (X2), dried over anhydrous magnesium sulphate, filtered and the filtrate evaporated to dryness. Chromatography of the residue on silica gel in 0→4% methanol in dichloromethane gave an oil, which, on treatment with an ethereal solution of hydrogen chloride, gave the title compound, m.p. 131°–3° C. (ethyl acetate-diethyl ether), as a 45:55 mixture of diastereoisomers.

¹H nmr δ(DMSO—d₆+D₂O): 1.15 (3H, d), 2.7–3.7 (7H, complex), 3.8 (3H, s), 4.05–4.3 (2H, m), 5.15 (1H, d), 7.3–7.6 (7H, m), 7.85–8.05 (2H, d).

EXAMPLE 4

4-[2-(2-[(3-Trifluoromethyl)phenyl]morpholino)propyl]phenoxyacetic acid methyl ester hydrochloride Thionyl chloride (15 ml) was added to a solution of N-[2-(4-carbomethoxymethoxyphenyl)-1-methylethyl]-2-(2-hydroxyethoxy)-2-(3-trifluoromethylphenyl)ethanamine (8 g) in toluene (100 ml) and the mixture stirred at room temperature for 45 minutes then thoroughly evaporated to dryness. Acetone (150 ml), potassium carbonate (15 g) and potassium iodide (50 mg) was added to the residue and the mixture heated under reflux, with stirring, for 17 hours, cooled, filtered and the filtrate evaporated to dryness. The residue was added to brine, extracted with dichloromethane (X2), and the combined extracts washed with brine, dried over anhydrous magnesium sulphate, filtered and the filtrate evaporated to dryness. Chromatography of the residue on silica gel in 0–4% methanol in dichloromethane gave an oil, which, on treatment with an ethereal solution of hydrogen chloride, gave the title compound, m.p. 204°–5° C. (methanol-ethyl acetate).

¹H nmr δ(DMSO—d₆): 1.2 (3H, d), 2.6–3.85 (10H, s on complex m), 4.15–4.5 (2H, d), 4.8 (2H, s), 5.3 (1H, d), 6.8–7.0 (2H, d), 7.1–7.3 (2H, d), 7.65–7.9 (4H, m), 12.3 (1H, broad; exchanges with D₂O).

The mother liquors from the above crystallisation were evaporated to dryness and subsequently used in Example 5.

EXAMPLE 5

4-[2-(2-[(3-Trifluoromethyl)phenyl]morpholino)propyl]phenoxy-N-methylacetamide hydrochloride The title compound, m.p. 204°–6° C. (ethyl acetate) was obtained from:
4-[2-(2-[(3-trifluoromethyl)phenyl]morpholino)propyl]phenoxyacetic acid methyl ester hydrochloride (obtained from the mother liquors of Example 4) by an analogous procedure to that described in Example 2.

¹H nmr δ(DMSO—d₆); 1.15 (3H, d), 2.55-2.85 (4H, d on m), 2.95-3.85 (6H, complex), 4.1-4.35 (2H, m), 4.4 (2H, s), 5.3 (1H, d), 6.85-7.05 (2H, d), 7.15-7.35 (2H, d), 7.6-7.9 (4H, m), 8.1 (1H, broad; exchanges with D₂O), 12.2 (1H, broad; exchanges with D₂O).

EXAMPLE 6

4-[2-(2-[3-Chlorophenyl]morpholino)propyl]phenoxyacetic acid methyl ester hydrochloride The title compound, m.p. 184°-5° C. (methanol-ethyl acetate), was obtained, as a single diastereoisomer, from N-[2-(4-carbomethoxymethoxyphenyl)-1-methylethyl]-2-(2-hydroxy ethoxy)-2-(3-chlorophenyl)ethanamine, by an analogous procedure to that described in Example 4.

¹H nmr δ(DMSO—d₆): 1.15 (3H, d), 2.5-2.85 (1H, m), 2.95-3.65 (6H, complex), 3.65 (3H, s), 4.1-4.3 (2H, m), 4.75 (2H, s), 5.15 (1H, d), 6.8-7.0 (2H, d), 7.1-7.3 (2H, d), 7.35-7.6 (4H, complex), 11.8 (1H, broad; exchanges with D₂O).

The mother liquor from the above recrystallisation was used to obtain a sample enriched in the second diastereoisomer, as described in Example 7.

EXAMPLE 7

4-[2-(2-[3-Chlorophenyl]morpholino)propyl]phenoxyacetic acid methyl ester hydrochloride The mother liquor from the recrystallisation, described in Example 6, was evaporated to dryness. Recrystallisation of the residue three times from ethyl acetate gave the title compound, m.p. 126°-9° C., as a 23:77 mixture of diastereoisomers.

EXAMPLE 8

4-[2-(2-[3-Chlorophenyl]morpholino)propyl]phenoxy-N-methylacetamide dihydrochloride hemihydrate The title compound, m.p. 161°-5° C. (methanol-ethylacetate-diethyl ether), was obtained, as a 77:23 mixture of diastereoisomers, from 4-[2-(2-[3-chlorophenyl]morpholino)propyl]phenoxyacetic acid methyl ester hydrochloride, by an analogous procedure to that described in Example 2.

¹H nmr δ(DMSO—d₆): 1.20 (3H, d), 2.5-2.9 (4H, complex), 3.0-3.9 (6H, complex), 4.1-4.4 (2H, m), 4.45 (2H, s), 5.25 (1H, d), 6.8-7.05 (2H, d), 7.1-7.35 (2H, d), 7.35-7.65 (4H, complex), 8.15 (1H, broad; exchanges with D₂O), 9.25 (2H, exchanges with D₂O), 12.2 (1H, broad; exchanges with D₂O).

EXAMPLE 9

N-Methyl-2-(4-[2-(2-[3-Chlorophenyl]morpholino)propyl]phenoxy)ethanamine dihydrochloride hemihydrate To a stirred solution of 4[2-(2-[3-chlorophenyl]morpholino)propyl]phenoxy-N-methylacetamide (3.6 g) in dry tetrahydrofuran (80 ml) was added borane-methyl sulphide complex (10 ml) in dry tetrahydrofuran (20 ml), under nitrogen. The solution was boiled under reflux for 4 hours, and, after cooling to room temperature, methanol (30 ml) was added carefully. This solution was allowed to stand overnight at room temperature, hydrogen chloride gas passed through for 10 mins, boiled under reflux for one hour, cooled and evaporated to dryness. Aqueous sodium carbonate was added to the residue and extracted with dichloromethane (×2). The combined organic extracts were washed with brine (×2), dried over magnesium sulphate, filtered and evaporated to dryness. Ethereal hydrogen chloride was added to the residue and the resultant solid recrystallised from methanol-ethyl acetate to give the title compound, m.p. 145°-55° C.

¹H nmr δ(DMSO—d₆): 1.05-1.3 (3H, d), 2.5-2.9 (4H, complex), 3.0-3.8 (9H, complex), 4.1-4.5 (4H, m), 5.2 (1H, d), 6.85-6.1 (2H, d), 7.15-7.3 (2H, d), 7.35-7.6 (4H, m), 9.55 (2H, exchanges with D₂O), 12.2 (1H, exchanges with D₂O).

EXAMPLE 10

4-[2-{N-(2-[3-Chlorophenyl]-hexahydro-1,4-oxazapine)}propyl]-phenoxyacetic acid methyl ester hydrochloride monohydrate The title compound was prepared as a mixture of diastereoisomers, mpt. 46°-50° C., from N-[2-(4-carbomethoxymethoxyphenyl)-1-methylethyl]-2-(3-hydroxypropoxy)-2-(3-chlorophenyl)ethanamine by an analogous procedure to that described in Example 4.

¹H nmr δ(DMSO—d₆): 1.10 (1.5H, d); 1.15 (1.5H, d); 2.1-2.2 (1H, m); 2.5-2.8 (1H, m); 3.2-3.8 (9H, complex m, 2H exchange with D₂O); 3.69 (3H, s); 3.9-4.0 (2H, m); 4.77 (2H, s); 5.1-5.3 (1H, m); 6.8-6.9 (2H, m); 7.1-7.2 (2H, m); 7.3-7.5 (4H, m); 11.0-11.3 (1H, broad m, exchanges with D₂O).

EXAMPLE 11

4-[2-(2-[2-Benzofuranyl]morpholino)propyl]phenoxyacetic acid methyl ester hydrochloride The title compound, m.p. 175°-187° C. (diethyl ether-methanol) was obtained, as a single diastereoisomer, from N-[2-(4-carbomethoxymethoxyphenyl)-1-methylethyl]-2-(2-hydroxyethoxy)-2-(2-benzofuranyl)ethanamine by an analogous procedure to that described in Example 4.

¹H nmr δ(DMSO—d₆): 1.18 (3H, d), 2.6-2.75 (1H, t), 3.35-3.7 (5H, m), 3.7 (3H, s), 3.3 (1H, d), 4.2 (2H, m), 4.77 (2H, s), 5.37 (1H, d), 6.9 (2H, d), 7.08 (1H, s), 7.21 (1H, d), 7.25-7.4 (3H, m), 7.6 (1H, d), 7.66 (1H, d), 11.85 (1H, broad; exchanges with D₂O).

The mother liquor from the above recrystallisation was used to obtain a sample enriched in the second diastereoisomer, as described in Example 12.

EXAMPLE 12

4-[2-(2-[2-Benzofuranyl]morpholino)propyl]phenoxyacetic acid methyl ester hydrochloride The mother liquor from the recrystallisation, described in Example 11, was evaporated to dryness. Recrystallisation of the residue from methanol-diethylether gave the title compound, m.p. 135°-144° C., as a 15:85 mixture of diastereoisomers.

EXAMPLE 13

4-[2-(2-[3-Chlorophenyl]morpholino)ethyl]phenoxyacetic acid methyl ester hydrochloride A mixture of 4-[2-(2-[3-chlorophenyl]morpholino)ethyl]anisole (2.6 g) in 48% aqueous hydrobromic acid (90 ml) was heated under reflux, with stirring, for 4 hours, cooled and evaporated to dryness. The residue was dissolved in acetone (80 ml), added to a mixture of anhydrous potassium carbonate (11 g), potassium iodide (50 mg) and methyl bromoacetate (1.5 ml) and the resultant mixture heated under reflux, with stirring, overnight. After cooling, filtering and evaporating the filtrate to dryness, the residue was dissolved in dichloromethane, washed with aqueous sodium carbonate (×2), brine (×1), dried (MgSO₄), filtered and evaporated to dryness. Chromatography of the residue on silica gel in 0–2% methanol in dichloromethane gave an oil, which, on treatment with an ethereal solution of hydrogen chloride, gave the title compound, m.p. 156°–7° C. (methanol-ethyl acetate).

¹H nmr δ(DMSO—d₆): 2.8–4.3 (13H, complex), 4.8 (2H, s), 5.1 (1H, m), 6.8–7.35 (4H, dd), 7.4–7.65 (4H, complex), 12.1 (1H, broad, exchanges with D₂O).

DESCRIPTION 1

4-[2-(2-[3-Chlorophenyl]morpholino)ethyl]anisole

Chloroacetyl chloride (1.0 ml) in dichloromethane (20 ml) was added dropwise to a mixture of triethylamine (4 ml) and N-[2-(4-methoxyphenyl)ethyl]-2-hydroxy-2-(3-chlorophenyl)ethanamine (3.5 g) in dichloromethane (50 ml) at 0° C., with stirring, over 15 minutes. After stirring for a further 90 minutes, the mixture was washed with dilute hydrochloric acid (×2), brine (×1), dried (MgSO₄), filtered and evaporated to dryness. The residue, in ethanol (50 ml), was added to sodium ethoxide (generated from sodium (0.4 g) and ethanol (80 ml)) and heated under reflux, with stirring, overnight. After cooling and evaporating to dryness, the residue was dissolved in dichloromethane, washed with brine (×1), dried (MgSO₄), filtered and evaporated to dryness to give the morpholinone as an oil.

The morpholinone (3.5 g) in dry diethyl ether (60 ml) was added dropwise to a suspension of lithium aluminium hydride (1.9 g) in dry diethyl ether (100 ml), with stirring, under nitrogen and the resultant mixture stirred overnight. After careful addition of water (2 ml), 10% aqueous sodium hydroxide (3 ml), and water (5 ml), and mixture was filtered, the filtrate dried (MgSO₄), filtered and evaporated to dryness. Chromatography of the residue on silica gel in 2% methanol in dichloromethane gave the title compound as an oil which was used without further purification.

DEMONSTRATION OF EFFECTIVENESS OF COMPOUNDS (a) Anti-hyperglycaemic activity

Female CFLP mice, weighing approximately 25 g, were fasted for 24 hours prior to the study. The compounds under study were administered orally as an aqueous solution to each of 6 mice. 30 minutes later a blood sample (10 μl) was obtained from the tail for the analysis of blood glucose. Immediately after taking this blood sample, glucose (1 g/Kg body weight) was administered subcutaneously to each mouse. 6 mice were given water as a control. Blood samples were then obtained from each mouse at 30 minute intervals for 120 minutes.

Compounds that produced a significant (P<0.05) reduction of blood glucose, compared with control mice given water, at any time interval, were considered active. The area under the blood glucose curve over the 2 hour period after the administration of the glucose was calculated for each compound and compared with the value for control animals.

| Compounds of Example No. | Dose (μmol/Kg) | % Reduction in area under Blood Glucose Curve |
|---|---|---|
| 1 | 12.5 | 50 |
| 2 | 25.0 | 39 |
| 3 | 25.0 | 32 |
| 4 | 5.0 | 39 |
| 5 | 5.0 | 34.5 |
| 6 | 0.2 | 46 |
| 7 | 0.1 | 19 |
| 8 | 0.2 | 44 |
| 10 | 2.5 | 31 |
| 13 | 10.0 | 42 |

(b) Effect on Energy Expenditure

The effect of the compounds on the energy expenditure of mice was demonstrated by means of the following procedure:

Female CFLP mice, each weighing approximately 24 g were given food and water ad lib before and during the experiment. The compounds were dissolved in water by addition of one mole of hydrochloric acid per mole of compound and these solutions were administered orally to each of 12 mice. A further 12 mice were dosed orally with water. The mice were placed in boxes through which air was drawn and the oxygen content of the air leaving the boxes was measured. The energy expenditure of the mice was calculated for 21 hours after dosing from the volume of air leaving the boxes and its oxygen content, following the principles described by J. B. de V. Weir, *J. Physiol.* (London), 109, 1–9 (1949). The results are expressed as a percentage of the rate of energy expenditure of the mice dosed with water.

| Compounds of Example No. | Dose mg/kg po | Mean Energy Expenditure | |
|---|---|---|---|
| | | (0–3 h) | (0–21 h) |
| 1 | 20.3 | 146 | 154 |
| 2 | 20.2 | 145 | 139 |
| 4 | 23.7 | 133 | 130 |
| 5 | 23.6 | 135 | 122 |
| 6 | 22.0 | 143 | 137 |
| 7 | 22.0 | 119 | 131 |
| 8 | 24.2 | 168 | 148 |
| 9 | 23.5 | 154 | 130 |
| 10 | 23.6 | 127 | 114 |
| 11 | 22.3 | 154 | 105 |
| 12 | 22.3 | 151 | 104 |

What is claimed is:

1. A compound of formula (I):

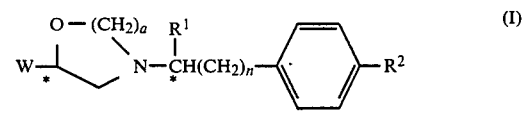

or a salt thereof, in which W is phenyl optionally substituted by halogen or trifluoromethyl, or a benzofuran-2-yl group, $R^1$ is hydrogen or methyl, and $R^2$ is a group O—E—NR³R⁴ wherein $R^3$ and $R^4$ each represents hydrogen or $C_{1-6}$ alkyl, n is 1 or 2, a is 2, and E is a $C_{2-7}$ straight or branched alkylene chain with at least two carbon atoms separating the two heteroatoms in the group $R^2$.

2. A compound according to claim 1, wherein $R^1$ is methyl.

3. A compound according to claim 1, wherein n is 1.

4. A compound according to claim 1 wherein E is CH$_2$CH$_2$.

5. A compound according to claim 1, which is: N-methyl-2-(4-[2-(2-[3-chlorophenyl]morpholino)-propyl]phenoxy)ethanamine.

6. A pharmaceutical composition comprising a compound of formula (I):

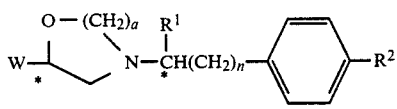

in which W is phenyl optionally substituted by halogen or trifluoromethyl, or a benzofuran-2-yl group, R$^1$ is hydrogen or methyl, and R$^2$ is a group O—E—NR$^3$R$^4$ wherein R$^3$ and R$^4$ each represents hydrogen or C$_{1-6}$ alkyl, n is 1 or 2, a is 2 and E is a C$_{2-7}$ straight or branched alkylene chain with at least two carbon atoms separating the two heteroatoms in the group R$^2$;

or a pharmaceutically acceptable salt thereof with a pharmaceutically acceptable carrier therefor.

7. A method for treating hyperglycaemia in a human or non-human animal which method comprises administering an effective, non-toxic amount of a compound of formula (I):

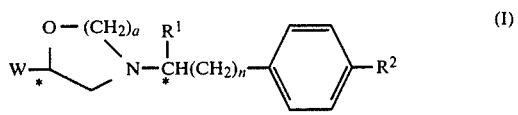

in which W is phenyl optionally substituted by halogen or trifluoromethyl, or a benzofuran-2-yl group, R$^1$ is hydrogen or methyl, and R$^2$ is a group O—E—NR$^3$R$^4$ wherein R$^3$ and R$^4$ each represents hydrogen or C$_{1-6}$ alkyl, n is 1 or 2 and a is 2, and E is a C$_{2-7}$ straight or branched alkylene chain with at least two carbon atoms separating the two heteroatoms in the group R$_2$;

or a pharmaceutically acceptable salt thereof to a hyperglycaemic human or non-human animal.

8. A method for treating obesity in human or non-human animals, which method comprises administering an effective, non-toxic amount of a compound of formula (I):

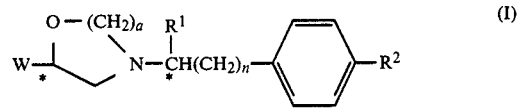

in which W is phenyl optionally substituted by halogen or trifluoromethyl, or a benzofuran-2-yl group, R$^1$ is hydrogen or methyl, and R$^2$ is a group O—E—NR$^3$R$^4$ wherein R$^3$ and R$^4$ each represents hydrogen or C$_{1-6}$ alkyl, n is 1 or 2, a is 2 and E is a C$_{2-7}$ straight or branched alkylene chain with at least two carbon atoms separating the two heteroatoms in the group R$^2$;

or a pharmaceutically acceptable salt thereof to an obese human or non-human animal.

* * * * *

UNITED STATES PATENT AND TRADEMARK OFFICE
CERTIFICATE OF CORRECTION

PATENT NO. : 4,665,072

DATED : May 12, 1987

INVENTOR(S) : Barrie C. C. Cantello

It is certified that error appears in the above—identified patent and that said Letters Patent is hereby corrected as shown below:

In the specification, above "Related U.S. Application Data", kindly insert the following:

--[30] Foreign Application Priority Data--

November 2, 1983 [GB] Great Britain ........... 8329247
February 16, 1984 [GB] Great Britain .......... 8404047

--

Signed and Sealed this

First Day of September, 1987

Attest:

DONALD J. QUIGG

*Attesting Officer*      *Commissioner of Patents and Trademarks*